United States Patent [19]
Morris

[11] Patent Number: 5,827,275
[45] Date of Patent: Oct. 27, 1998

[54] ELECTRO-SURGICAL INSTRUMENT AND FABRICATION METHOD

[75] Inventor: James R. Morris, Sedalia, Colo.

[73] Assignee: MediCor Corporation, Wheeling, Ill.

[21] Appl. No.: 718,626

[22] Filed: Sep. 16, 1996

Related U.S. Application Data

[63] Continuation-in-part of Ser. No. 943,223, Sep. 9, 1992, Pat. No. 5,562,659.

[51] Int. Cl.⁶ .................................................... A61B 17/39
[52] U.S. Cl. ............................... 606/41; 600/372; 606/45
[58] Field of Search ................................ 606/41, 45–50; 128/642; 600/372

[56] References Cited

U.S. PATENT DOCUMENTS

| | | |
|---|---|---|
| 4,228,800 | 10/1980 | Degler, Jr. et al. . |
| 4,726,368 | 2/1988 | Morris . |
| 4,785,807 | 11/1988 | Blanch ...................................... 606/45 |
| 4,850,353 | 7/1989 | Stasz et al. . |
| 5,047,026 | 9/1991 | Rydell ...................................... 606/48 |
| 5,221,281 | 6/1993 | Klicek . |
| 5,281,216 | 1/1994 | Klicek . |
| 5,382,247 | 1/1995 | Cimino et al. ............................. 606/45 |
| 5,562,659 | 10/1996 | Morris ...................................... 606/41 |

OTHER PUBLICATIONS lMcPherson, R. et al., "Elastic Anisotropy of APS Alumina Coatings and Its Relationship to Microstructure," pp. 277–290, *High Performance Ceramic Films and Coatings*, Vincenzini (Ed.), Elsevier Science Publishers B.V. (1991).

Bajaguram H. et al., "Anisotropy of Thermally Spray ed Coatings," pp. 1011–1017, Proceedings of the International Thermal Spray Conference & Exposition, Orlando, Florida, USA (28 May–5 Jun. 1992).

Vuoristo, P.M.J. et al., "On the Properties of Detonation Gun Sprayed and Plasma Sprayed Ceramic Coatings," pp. 171–175, Proceedings of the international Thermal Spray Conference & Exposition, Orlando, Florida, USA (28 May–5 Jun. 1992).

Kuroda, S. et al., Journal of Thermal Spray Technology 1(4):325–332 (Dec. 1992).

McPerson et al, "Elastic Anisotropy . . . To Microstructure", pp. 277–290, High Performance Ceramic Films and Coatings, Vincenzini (Ed.), Elsevier Science Publishers B.V., 1991.

Vuoristo et al "On The Properties . . . Coatings", pp. 171–175, Proceedings of the International Thermal Spray Conference and Exposition, Orlando, FL, 1992.

*Primary Examiner*—Michael Peffley
*Attorney, Agent, or Firm*—Olson & Hierl, Ltd.

[57] ABSTRACT

An exceptionally durable electrical insulation coating for electro-surgical instruments is provided. The insulation coating is ceramic and exhibits excellent insulative properties in the 500 KHZ to 1 MHZ frequency range. This feature drastically reduces, if not totally eliminates, many problems of current electrical insulation materials used in electrosurgery. The insulating ceramic coating can be readily applied by plasma deposition techniques to new or existing mono/bipolar surgical instruments. The insulating ceramic coating is thermally sprayed, anisotropic, and exhibits a Young's Modulus value of no more than about $30 \times 10^6$ psi parallel to the coating plane.

15 Claims, 2 Drawing Sheets

ELECTRO-SURGICAL INSTRUMENT AND FABRICATION METHOD

CROSS-REFERENCE TO RELATED APPLICATION

This application is a continuation-in-part of U.S. Ser. No. 07/943,223, filed on Sep. 9, 1992, now U.S. Pat. No. 5,562,659.

FIELD OF THE INVENTION

This invention relates to electro-surgical instruments and apparatus and more particularly to electro-surgical instruments with ceramic deposited insulative coating.

BACKGROUND OF THE INVENTION

Since the inception of the monopolar and bipolar electro-surgical instruments for cutting and coagulating tissues, numerous cases of inadvertent and unwanted electrical shocks and burns to the patient and physician, and even deaths to patients, have been reported. In a great number of these reports, the cause of the reported injury was specified as resulting from the breakdown of the electro-surgical instrument's insulation.

The insulation material typically utilized has been poly (tetrafluoroethylene) (Teflon), poly(vinyl chloride) (PVC), or heat-shrinkable plastic materials. While these materials do have exceptionally well-documented electrical insulative characteristics, they are severely lacking as ideal insulators for surgical instruments. The primary reasons for this are that they have very little abrasion resistance (i.e., the coating wears off easily). In addition, they can be scratched easily, leaving areas with bare metal exposed. They degrade rapidly with various sterilization methods, causing insulative properties to deteriorate; and additionally, they can retain moisture between bare metal and insulation, thus contributing to problems of corrosion and to problems with sterilization.

Also, they have low resistance to heat. The insulation degrades with heat generated by wattage flowing through the instrument during prolonged use. Finally, the currently utilized instrument insulations must be replaced regularly which results in excessive costs to health care providers.

It is the applicant's belief after analysis of the technology that the ideal insulator for electro-surgical instruments would have at least the following characteristics. It should have excellent dielectric (insulative) properties in the 500 KHZ to 1 MHZ frequency range which is typical of electrosurgery unit generators. In addition, it should have exceptional wear and abrasion characteristics, and should be impervious to scratching, nicking or cutting. It should be chemically inert and sterilizable, non-toxic, non-irritating, and non-cytotoxic, and be acceptable for use in the human body. It should adhere rigidly to the base metal of the instrument to prevent corrosion and sterility problems. It should be cost effective and it should be unaffected by various sterilization techniques, and, finally, it should be readily applicable to a variety of shapes and sizes of surgical instruments.

Electro-surgical instruments that embody the present invention achieve the foregoing characteristics by utilizing a thermally sprayed ceramic coating. Unlike molded and sintered ceramics such as ceramic insulating panels or wafers, thermally sprayed ceramic coatings are relatively more flexible and are characterized by anisotropic elastic properties. That is, the elastic properties of the resulting material determined parallel to the coating plane are different from those determined perpendicular to the coating plane. See, for example, Nakahira et al., "Anisotropy of Thermally Sprayed Coatings," Proceedings of the International Thermal Spray Conference and Exposition, Orlando, Fla., USA, 28 May-5 Jun. 1992, pp. 1011–1017.

SUMMARY OF THE INVENTION

An electro-surgical instrument having excellent electrical insulative properties comprises a roughened stainless steel substrate and a durable, continuous, thermally sprayed ceramic coating thereon. The coating has a dielectric strength greater than 3,000 volts/mm in the frequency range of 500 KHZ to 1 MHZ and a metallographic porosity of less than one volume percent. The stainless steel substrate preferably has a round transverse cross-section. The thermally sprayed ceramic coating has a Young's Modulus value of no more than about $30 \times 10^6$ pounds per square inch parallel to the coating plane and a Young's Modulus anisotropy coefficient of at least about 2.

The ceramic coating is applied to the roughened stainless steel substrate by thermal spraying, preferably using a plasma gun, a detonation gun, or a high-velocity oxygen fuel system.

DESCRIPTION OF PREFERRED EMBODIMENTS

Figure 1:
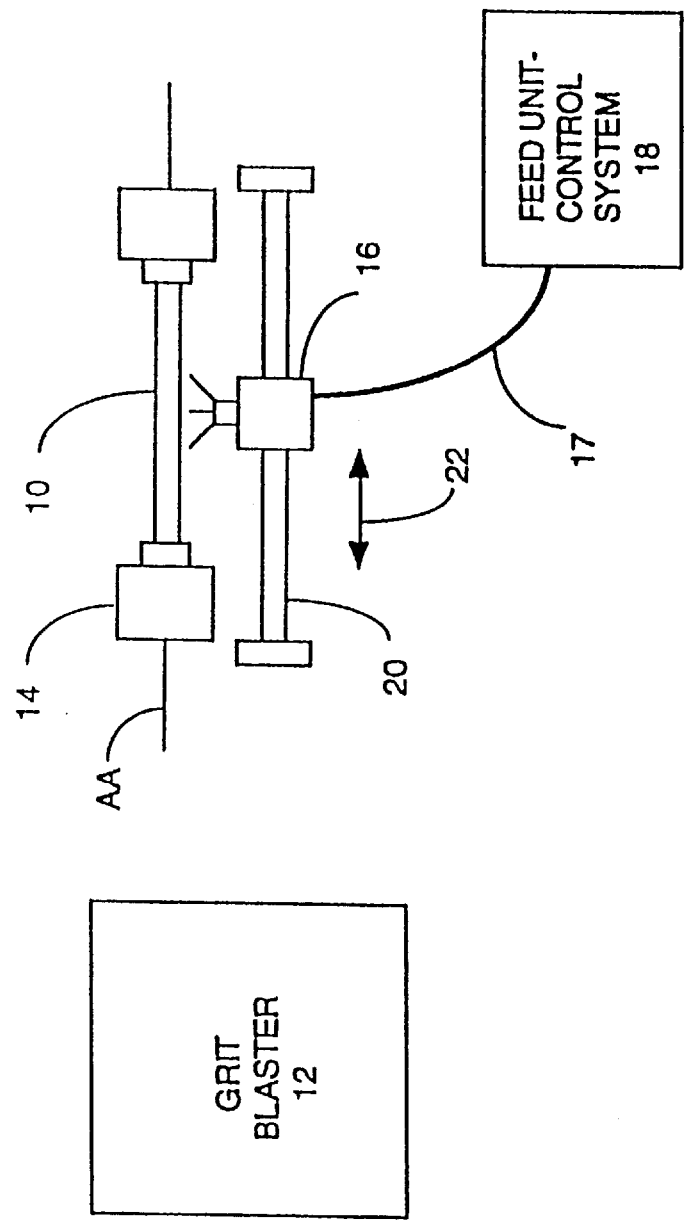
FIG. 1 is a schematic illustration of apparatus for applying an electrical insulation coating to an electro-surgical instrument.

Through utilization of a plasma gun, detonation gun, or a high velocity oxygen feed (HVOF) system for ceramic deposition coating, the aforementioned desirable characteristics have been achieved. The particular ceramic of choice for the present thermal spray coatings is $Al_2O_3$ (aluminum oxide), although magnesium oxide, zirconia-yttria, zirconia-calcia, or the like coating can also be utilized. The $Al_2O_3$ coating material has an inherently greater dielectric strength and, therefore, allows thinner coating to achieve the same insulative capacity as the other commonly used materials when applied in thicker coating.

Additionally, in contradistinction to molded ceramic panels, thermal spray coatings are more elastic, i.e., have a relatively lower Young's Modulus[1], that permits the use of such coatings on flexible or flexing parts of electrosurgical instruments.

[1]The well known Young's Modulus is defined as the ratio of stress to strain in the elastic range of the material. The higher the Young's Modulus of a material, the stiffer is that material.

The presently contemplated electro-surgical instruments are provided with an anisotropic thermally sprayed ceramic coating that exhibits a Young's Modulus of no more than abut $30 \times 10^6$ pounds per square inches (psi), preferably no more than $15 \times 10^6$ psi, in a direction parallel to the coating plane. For the presently contemplated thermally sprayed ceramic coatings the Young's Modulus anisotropy coefficient is at least 2, and preferably is about 3. Particularly preferred thermally sprayed ceramic coatings for electrosurgical instruments are aluminum oxide coatings having a Young's Modulus of no more than about $15 \times 10^6$ pounds per square inch and a Young's Modulus anisotropy coefficient of about 3.

The preferred thickness of the coating for most surgical instrument applications has been found to be 0.01 to 0.015 inch. Coatings in this thickness range have been tested and found to be excellent insulators up to at least 4–6 kilovolts, 3,000–4,000 volts alternating current RMS. Relatively thinner or relatively thicker coatings can also be applied depending upon the particular ceramic material being used.

DC current leakage at 3,000 volts has been tested and found to be less than 100 micro amperes.

Coatings of $Al_2O_3$ have been tested and found to be non-toxic, non-cytotoxic, and non-irritating.

The preferred coating has also been found not to degrade through repeated sterilization methods of chemical soak, steam and autoclave sterilization.

This coating has also been wear and abrasion tested by placing coated samples in a rock tumbler device for 24 hours. This is roughly equivalent to 3–4 hours on a grinding wheel. The results of this test indicated that less than $\frac{1}{1000}$ of an inch of coating material was removed.

Further tests designed to indicate the coating's resistance to scratching and nicking have been performed through purposeful and continual scratching and cutting of the coating with stainless steel scalpel blades and scissor blades. Because the $Al_2O_3$ coating is so much harder than the typical stainless steel, no cuts or scratches were obtained. Instead, the metal of the stainless steel blades was worn off by the coating.

The characteristics of this coating lead to significant cost savings to users through eliminating the additional expenses of replacing typical fluorocarbon (Teflon) and plastic based insulation materials.

In addition, due to the combination of characteristics described, a significantly safer instrument is produced. Hospital and physician risk are decreased as well.

FIG. 1 illustrates a method for providing an insulation coating on a round electro-surgical instrument 10, such as a reusable endoscopic electrode having a round shaft in length about 16 inches and with a diameter of 0.065 inch. Instrument 10 is constructed from surgical stainless steel. Initially the instrument is masked to cover areas thereon which are not to be coated. The masking may be performed manually using conventional masking tape.

The instrument is next placed in a conventional grit blaster 12, such as, for example, that sold under the product designation Trinco Dry Blast Sand Blaster 36-BP2 which is commercially available from Trinity Tool Company, 34600 Commerce Road, Fraser, Minn. 48026. The surface of the instrument is cleaned and slightly roughened by the grit blaster.

The instrument is next mounted on a spindle assembly 14 with the longitudinal axis of the instrument coaxially aligned with the axis of rotation AA of the spindle assembly 14.

A coating applicator system which may comprise a plasma gun 16 connected by feed conduit 17 to material feed and control unit 18 is provided for spraying coating material in a plasma state onto the surface of the instrument. The coating applicator system may be an applicator system of a conventional type well known in the art such as, for example, that sold under the product designation Plasmatron® Thermal Spray System Model #3700-$B_2$B-100-D which is commercially available from Miller Thermal, Inc., Plasmadyne and Mogul Products, 555 Communication Drive, P.O. Box 1081, Appleton, Wis. 54912. Coating material which is to be applied to an instrument 10 is initially placed in the material feed unit 18 in a powdered form. Powdered forms of the materials which may be used in the coating process, including aluminum oxide, an aluminum oxide and titanium dioxide mixture, and molybdenum are commercially available under the product designations AI-1010 F, AI-1070, and AI-1138, respectively, from Alloys International Products, 1901 Ellis School Road, Baytown, Tex. 77521.

The spindle assembly 14 is positioned with its axis of rotation AA parallel to a guide assembly 20 which is adapted to support plasma gun 16 thereon for reciprocal motion 22. The tip of the gun 16 may be positioned 3.5 in. from the surface of the instrument 10. In a typical application the gun may be reciprocated back and forth at an average speed of approximately 1 ft./sec. and the instrument may be rotated by the spindle about axis AA at a rate of approximately 250 revolutions per minute. Cooling air may be applied to the instrument as from adjacent air jet nozzles (not shown) to cool the coating material after it is applied to the instrument.

Figure 2:
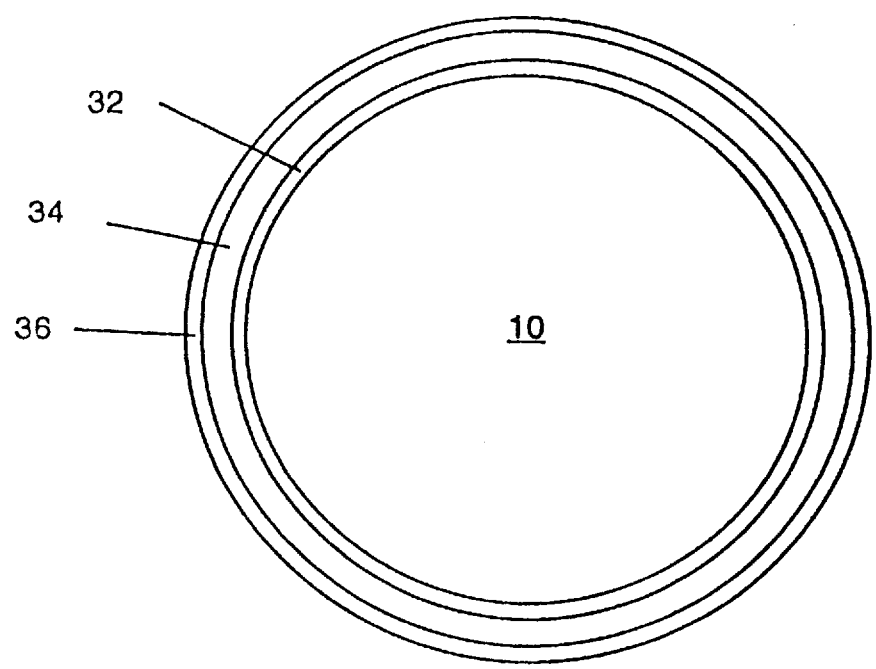
FIG. 2 is a cross-sectional view of an electro-surgical instrument with an insulation coating.

Although a coated instrument having the wear and insulating properties described elsewhere herein may be obtained through direct application of a single coating layer, such as a layer of aluminum oxide, to the instrument, in a preferred embodiment of the invention, shown in FIG. 2, three separate coatings are applied to the round shaft of the instrument: a bonding layer 32 (which may be molybdenum-powder #AI-1138 having a thickness of 0.001 in.), an insulative protection layer 34 (which may be aluminum oxide-powder #AI-1010 F having thickness of 0.020 in.), and a color (black) layer 36 (which may be aluminum oxide and titanium dioxide-powder #AI-1070 having a thickness of 0.001 in.). The bonding layer 32 improves the bonding of the insulative layer 34 to the instrument. The color layer may be applied to reduce glare from the instrument when it is used in a surgical procedure. After the ceramic coatings have been applied, a moisture barrier sealing layer may be applied to the instrument. One manner of applying a sealing layer is to hand-rub the instrument with silicone sealant such as a silsesquioxane or the like, and then heat the instrument, e.g., with four 175-Watt lamps, for about 30 minutes. Thereafter, excess sealant is removed by scrubbing and wiping the instrument with acetone.

Specific production parameters for the different powders listed above for use with the equipment described above are provided in Table 1, below.

TABLE 1

| | Parameters for Plasmatron ® Thermal Spray System | | |
|---|---|---|---|
| Operating Mode | Powder No. AI-1010F Sub-Sonic 40 KW | Powder No. AI-1138 Sub-Sonic 40 KW | Powder No. AI-1070 Sub-Sonic 40 KW |
| Spray Gun | SG-100 | SG-100 | SG-100 |
| Anode | 2083-155 | 355 | 155 |
| Cathode | 1083A-112 | 112 | 112 |
| Gas Injector | 2083-113 | 113 | 113 |

TABLE 1-continued

Parameters for Plasmatron ® Thermal Spray System

| Operating Mode | Powder No. AI-1010F<br>Sub-Sonic 40 KW | Powder No. AI-1138<br>Sub-Sonic 40 KW | Powder No. AI-1070<br>Sub-Sonic 40 KW |
|---|---|---|---|
| Nozzle # | N/A | N/A | N/A |
| Operating Parameters | | | |
| Power | | | |
| Open Circuit Voltage | N/A | N/A | N/A |
| Operating Voltage | 34.6 | 42 | 40 |
| Operating Current | 900 | 800 | 800 |
| Arc Gas/Primary | Argon | Argon | Argon |
| Flow Rate | N/A | N/A | N/A |
| Critical Orifice No. | 56 | 56 | 56 |
| Press. Reg. $P_1$, psig | 50 | 50 | 50 |
| Auxiliary Gas/Secondary | Helium | Helium | Helium |
| Flow Rate | N/A | N/A | N/A |
| Critical Orifice No. | 80 | 80 | 80 |
| Press. Reg. $P_1$, psig | 100 | 100 | 100 |
| Powder Gas/Carrier | Argon | Argon | Argon |
| Flow Rate | N/A | N/A | N/A |
| Critical Orifice No. | 77 | 77 | 77 |
| Press. Reg. $P_1$, psig | 40 | 50 | 50 |
| Hopper Setting/RPM | 2.5 | 1.3 | 3.5 |
| Powder Port | N/A | N/A | N/A |
| Meter Wheel/RPM | 2.5 | 1.3 | 3.5 |
| Spray Distance | 3.5 in. | 3.5 in. | 3.5 in. |

In addition to the aforementioned plasma gun coating procedures, other coating procedures known in the ceramic arts such as detonation guns and high-velocity oxygen fuel systems could also be used. A plasma gun is currently the best mode contemplated for applying a coating, however.

When nonuniform articles are to be coated, the article may be held manually as with tongs and manually rotated and reciprocated in front of a ceramic applicator gun. Instruments coated with ceramic in the manner described above were tested and evaluated as described below. The same procedure as described above may be used to apply a coating of magnesium oxide, zirconia-yttria, or zirconia-calcia rather than aluminum oxide to form an insulative coating.

The durability is first evaluated. Samples of a ceramic composite coating are processed in a rock tumbler device for 25 hours. This amount of wear is roughly equivalent to the wear which would be produced by 3–4 hours on a grinding wheel. The ceramic coating was not chipped or cracked after this treatment. From visual analysis under high magnification, it can be estimated that less than 1/1000 of an inch of coating material is removed during the experiment.

The toxicology is next studied. The results of toxicological evaluation of coated stainless steel samples are shown in Table 2, below.

TABLE 2

Toxicology Results

| Percent inhibition of cell growth<br>QCOP L300 | Non-inhibitory |
|---|---|
| Medium eluate method<br>QCOP L305 | Non-cytotoxic |
| Agar overlay<br>QCOP L303 | Non-cytotoxic |
| USP intracutaneous irritation<br>QCOP B309 | |
| Normal saline extract | Non-irritating |
| Cottonseed oil extract | Non-irritating |

TABLE 2-continued

Toxicology Results

| USP mouse systemic injection<br>QCOP B305 | |
|---|---|
| Normal saline extract | Non-toxic |
| Cottonseed oil extract | Non-toxic |
| Rabbit subcutaneous implantation | Non-irritating |

Electrical insulative properties are next considered. Table 3, below, illustrates the properties of the electrical insulative coating.

TABLE 3

Physical Properties of the Electrical Insulative Coating

| Application | Two coat plasma deposition |
|---|---|
| Insulative capacity | Greater than 3,000 V/mm |
| MOHS Hardness Scale<br>(Diamond hardness = 10.0) | 9.2 |
| Tensile bond strength (psi) | >8,000 |
| Modulus of rupture (psi) | 19,000 |
| Modulus of elasticity ($10^6$ psi)<br>(parallel to coating plane) | 11 |
| Density (q/cm$^3$) | 3.6 |
| Metallographic porosity<br>(volume %) | <1 |
| Surface Finish As-coated<br>(microinch rms) | 150 |

While illustrative and presently preferred embodiments of the invention have been described in detail herein, it is to be understood that the inventive concepts may be otherwise variously embodied and employed and that the appended claims are intended to be construed to include such variations except insofar as limited by the prior art.

I claim:

1. An electro-surgical instrument comprising:
   (a) a surgical instrument having a roughened stainless steel substrate; and (b) a durable, continuous thermally sprayed ceramic coating on said roughened stainless steel substrate, said coating providing electrical insulative properties to said substrate in the 500 KHZ to 1 MHZ frequency range greater than 3,000 volts/mm and having a metallographic porosity of less than one volume percent; said thermally sprayed ceramic coating having a Young's Modulus of no more than about $30 \times 10^6$ pounds per square inch parallel to the coating plane, and a Young's Modulus anisotropy coefficient of at least about 2.

2. The instrument of claim 1, said ceramic being selected from the group consisting of aluminum oxide, magnesium oxide, zirconia-yttria and zirconia-calcia.

3. The instrument of claim 1, wherein the thickness of said ceramic coating is about 0.01 to about 0.03 inch.

4. The instrument of claim 1, wherein a molybdenum bonding layer is present between said substrate and said ceramic coating.

5. The instrument of claim 1, wherein a molybdenum bonding layer is present between said substrate and said ceramic coating, and wherein an aluminum oxide and titanium dioxide color layer is present over said ceramic coating.

6. The instrument of claim 1 wherein a silicone sealant layer is present over said ceramic coating.

7. The instrument of claim 1, wherein said thermally sprayed ceramic coating has a Young's Modulus of no more than about $15 \times 10^6$ pounds per square inch parallel to the coating plane.

8. The instrument of claim 1, wherein said thermally sprayed ceramic coating has a Young's Modulus anisotropy coefficient of about 3.

9. The instrument of claim 1, wherein said thermally sprayed ceramic coating is an aluminum oxide coating having a Young's Modulus of no more than about $15 \times 10^6$ pounds per square inch parallel to the coating plane, and a Young's Modulus anisotropy coefficient of about 3.

10. The instrument of claim 1, wherein said roughened steel substrate has a round transverse cross-section.

11. An electro-surgical instrument operably associated with an electrosurgery frequency generator and comprising:
    (a) a surgical instrument with a round shaft providing a roughened stainless steel substrate; and
    (b) a durable, continuous, thermally sprayed, anisotropic ceramic coating on said stainless steel substrate providing electrical insulative properties to said substrate in the 500 KHZ to 1 MHZ frequency range greater than 3,000 volts/mm and having a metallographic porosity of less than 1 volume percent; said thermally sprayed ceramic coating having a Young's Modulus of no more than about $15 \times 10^6$ pounds per square inch parallel to the coating plane, and a Young's Modulus anisotropy coefficient of at least about 2.

12. A method of providing durable electrosurgical instrument insulation with excellent insulative properties in the 500 KHZ to 1 MHZ frequency range, comprising:
    (a) providing an electro-surgical instrument having a roughened surface; and
    (b) depositing on the roughened surface of said electro-surgical instrument, by thermal spraying, a continuous ceramic coating having a substantially uniform thickness sufficient to provide an insulative capacity of at least about 3000 volts/mm.

13. The method of claim 1, wherein said ceramic coating is applied using a system selected from the group consisting of a plasma gun, a detonation gun, and a high velocity oxygen fuel system.

14. The method of providing electro-surgical instrument insulation according to claim 1, comprising depositing said ceramic which is a member of the group consisting of aluminum oxide, magnesium oxide, zirconia-yttria and zirconia-calcia.

15. The method of providing electro-surgical instrument insulation according to claim 1, comprising depositing a thickness of said ceramic coating of about 0.01 inch to about 0.015 inch.

* * * * *